US00PP35450P2

(12) United States Plant Patent
Vikos

(10) Patent No.: US PP35,450 P2
(45) Date of Patent: Oct. 31, 2023

(54) ***EPIPREMNUM* PLANT NAMED 'EM0002'**

(50) Latin Name: *Epipremnun aureum*
Varietal Denomination: EM0002

(71) Applicant: EMMA'S GARDEN GROWERS, INC., Huntington, NY (US)

(72) Inventor: Ariel M. Vikos, North Merrick, NY (US)

(73) Assignee: Emma's Garden Growers, Inc., Huntington, NY (US)

( * ) Notice: Subject to any disclaimer, the term of this patent is extended or adjusted under 35 U.S.C. 154(b) by 0 days.

(21) Appl. No.: 17/803,714

(22) Filed: Oct. 26, 2022

(51) Int. Cl.
*A01H 5/00* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/00; A01H 5/12
See application file for complete search history.

*Primary Examiner* — Kent L Bell

(57) ABSTRACT

A new and distinct *Epipremnum* plant named 'EM0002' particularly distinguished by a unique leaf coloration appearing layered within the epidermis with creamy yellow to yellow being the background layer, a mix of lightly mottled shades of green and greyish green being the middle layer, and dark green areas flanking the leaf midrib and leaf margin being prominently the top layer, and a leaf shape that is wider and a more rounded oval with a heart shaped base, is disclosed.

3 Drawing Sheets

Figure 1:
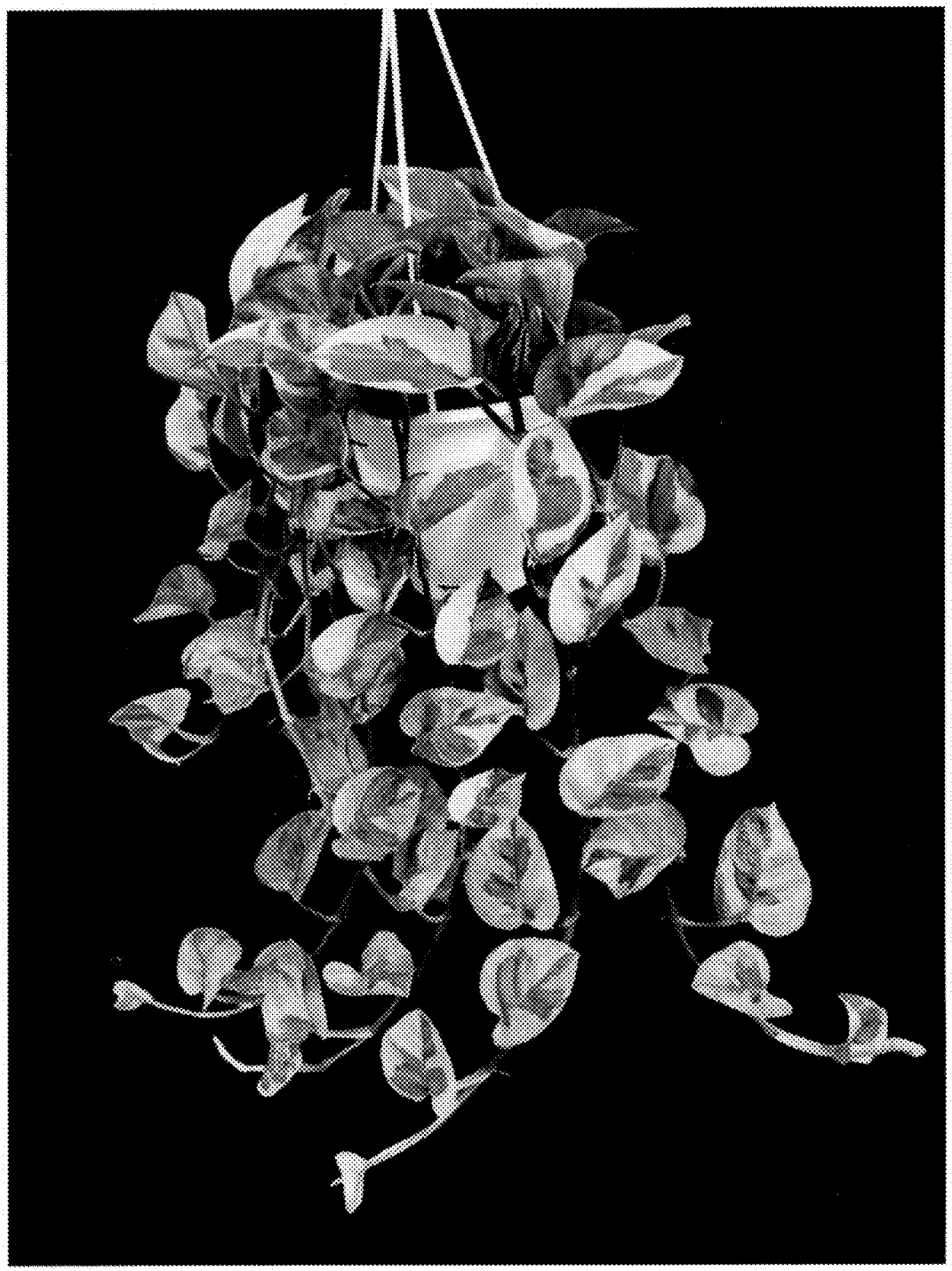

Genus and species: *Epipremnun aureum.*
Variety denomination: 'EM0002'.

BACKGROUND OF THE NEW PLANT

The present invention comprises a new and distinct variety of pothos plant, botanically known as *Epipremnun aureum*, and hereinafter referred to by the variety name 'EM0002'.

This new pothos plant was discovered by the inventor as a naturally occurring branch mutation from the *Epipremnum* plant named 'NJOY' (U.S. Plant Pat. No. 19,965) which was derived from vegetative tip cuttings and grown in a greenhouse in Melville, New York. The discovery of the new plant was made by the inventor in March 2021 in a non-publicly accessible area of a commercial greenhouse located in Melville, New York.

'EM0002' was first reproduced asexually using vegetative tip cuttings in Melville, New York in March 2021. Asexual propagation by vegetative tip cuttings of the new variety has shown that the unique features of the new variety are stable and reproduced true-to-type to date through four successive generations.

Plant Breeder's Rights for this variety have not been applied for. 'EM0002' has not been made publicly available or sold anywhere in the world more than one-year prior to the effective filing date of this application.

SUMMARY OF THE INVENTION

The new pothos variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new pothos variety. The combination of these characteristics distinguishes 'EM0002' as a new and distinct variety of pothos:

1. Irregular sized patches of dark green flanking both sides of the leaf midrib and sometimes appearing faintly along the leaf margins; dark green patches appearing along the leaf midrib are sometimes narrow, showing more of the background coloration, or sometimes appear across most of the leaf surface.
2. Leaf coloration appearing layered within the epidermis with creamy yellow to yellow being the background layer, a mix of lightly mottled shades of green and greyish green being the middle layer, and dark green patches flanking the leaf midrib and leaf margin being prominently the top layer.
3. A leaf shape that is wider and a more rounded oval with a heart shaped base.

DESCRIPTION OF THE PHOTOGRAPHS

This new pothos variety is illustrated by the accompanying-colored photographs which show the overall appearance and distinct characteristics of the plant. The colors shown are as true as can be reasonably obtained by conventional photographic procedures. The photographs are of 1-year-old plants grown in 6-inch round containers under moderate shade in a glass covered greenhouse in Melville, New York. Colors in the photographs may differ slightly from the color values cited in the botanical description which accurately describes the colors of the new variety.

FIG. 1. shows the overall plant form and foliage of 'EM0002'.

Figure 2:
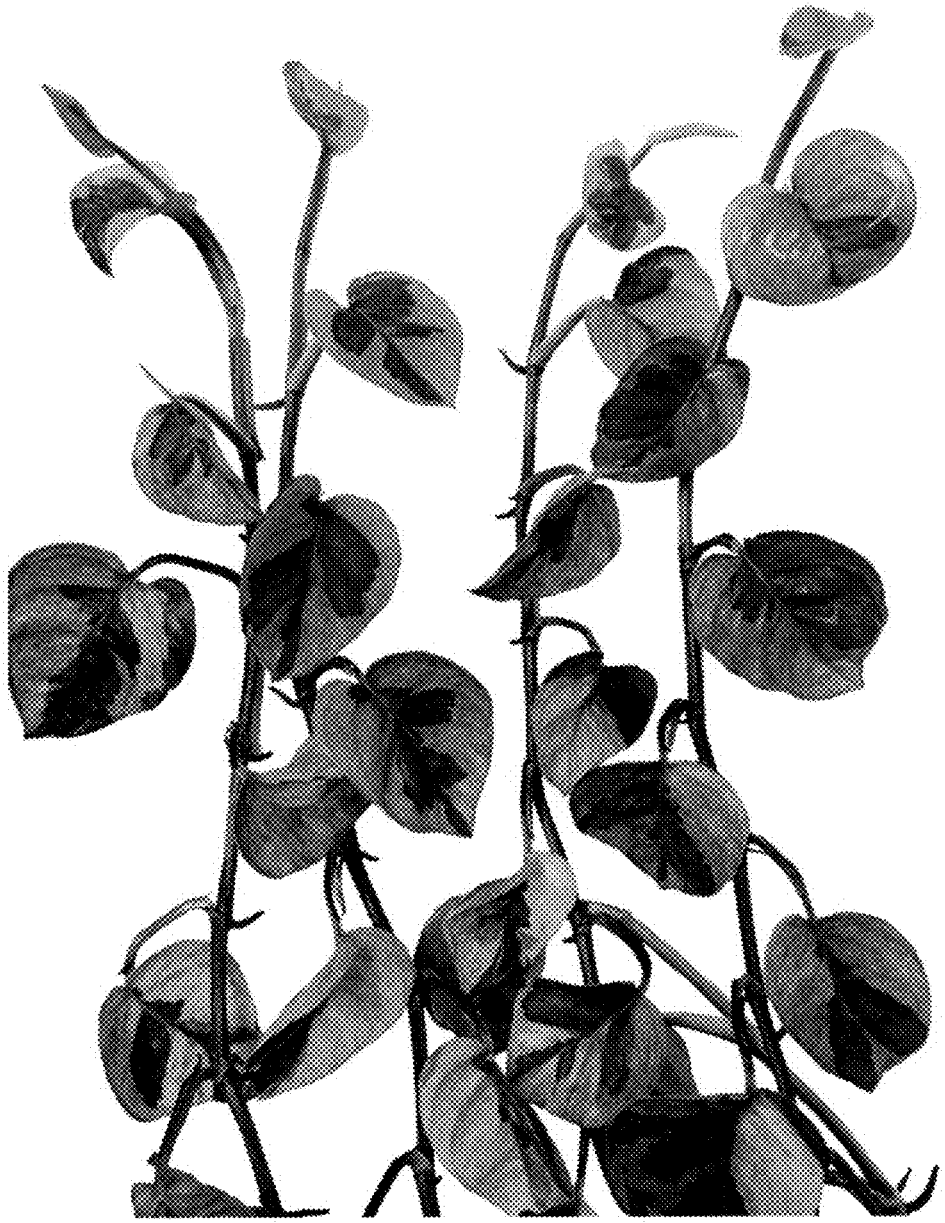

FIG. 2. shows typical vines and leaves of 'EM0002'.

Figure 3:
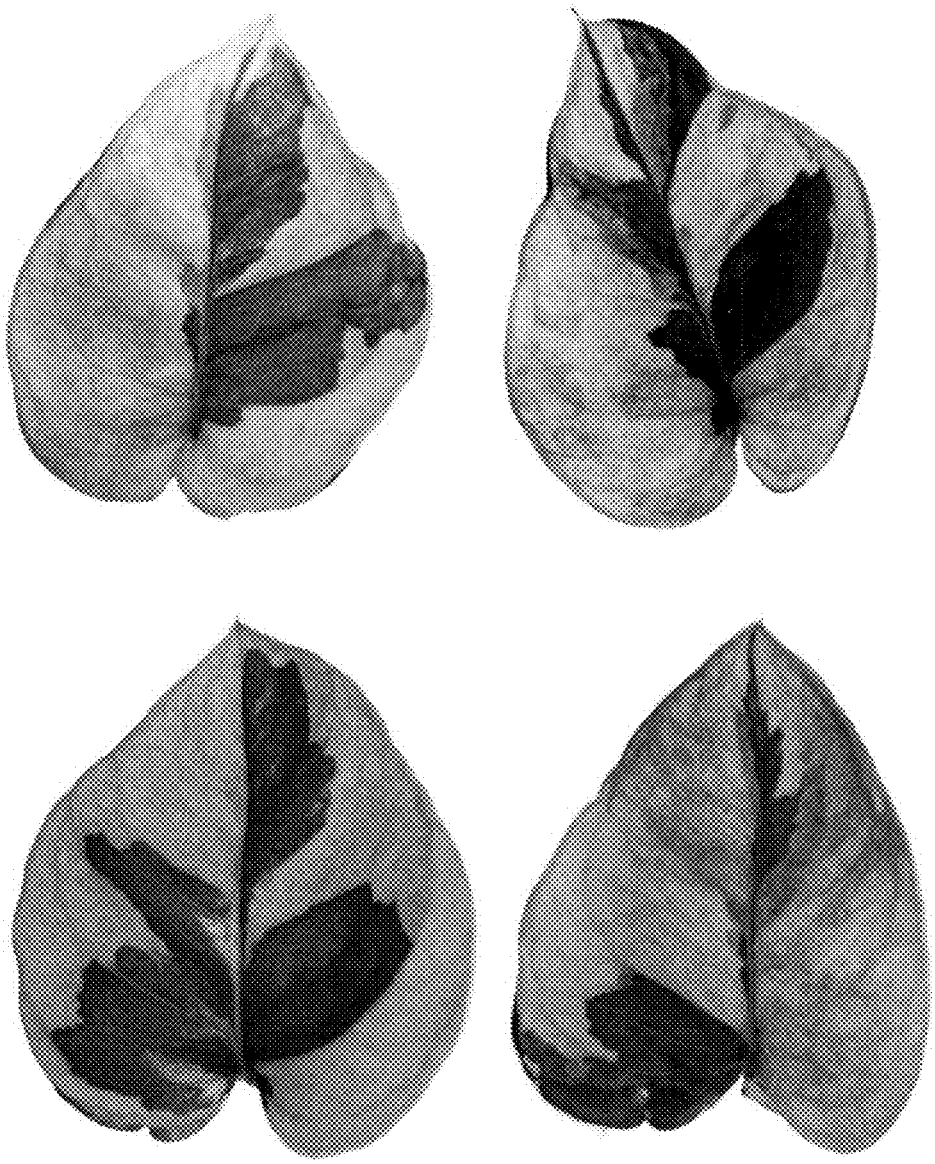

FIG. 3. shows typical leaf coloration patterns on the adaxial surface of mature leaves of 'EM0002'.

DESCRIPTION OF THE NEW VARIETY

In the following description, color references are made to The Royal Horticultural Society Colour Chart, Sixth Edition, except where general color terms of ordinary dictionary significance are used. The following observations and measurements describe plants grown under moderate shade in a glass covered greenhouse in Melville, New York. Detailed descriptions were taken in August 2022 from a 1-year-old plant grown in a 6-inch round container. Measurements and numerical values represent averages of typical plant types. Leaf color designations and the size and position of the color patches in the forthcoming examples describe typical leaves observed on plants of 'EM0002', but are not meant to be exhaustive of all variations of leaf color patterning observed on plants of 'EM0002'.

DETAILED BOTANICAL DESCRIPTION

Classification:

*Family.*—Araceae.

*Botanical.*—*Epipremnun aureum.*

*Common.*—Pothos.

*Denomination.*—'EM0002'.

General description:

*Plant type.*—Perennial tropical vine.

*Growth habit.*—Semi-compact and trailing.

*Height from soil level to top of foliar plane.*—8.80 cm.

*Growth rate.*—Vigorous.

*Branching characteristics.*—One main stem (vine), weak basal branching.

*Vine length.*—81.25 cm to 83.75 cm on a one-year-old vine.

*Vine diameter.*—0.64 cm at the proximal end, tapering to 0.18 cm at the distal end.

*Internode length.*—3.81 cm to 4.45 cm.

*Texture of stems.*—Rugose.

*Color of stems.*—139A (dark yellowish green) at the proximal end, gradually lightening to 145D (light yellow green) at the distal end.

*Number of leaves per stem.*—About 20 on a one-year-old vine.

*Propagation type.*—Vegetative tip cuttings.

*Time to produce a rooted cutting.*—20 days.

Foliage description:

*Arrangement.*—Alternate, simple.

*Attachment.*—Petiolate.

*Leaf.*—Shape: Mostly cordate with immature leaves occasionally deltate. Length: Mature leaf: 7.62 cm. Immature leaf (newly expanded): 5.08 cm to 6.35 cm. Width: Mature leaf: 5.08 cm to 6.35 cm. Immature leaf (newly expanded): 2.54 cm to 3.18 cm. Aspect: Immature leaves are folded downwards from about the center to the apex, mature leaves are predominantly concave. Apex shape: Acute to broadly accuminate. Base shape: Lobate, open area between lobes is shallow, about 0.64 cm in depth. Texture (both upper and lower surfaces): Highly rugose, velvety. Orientation: Held horizontal to slightly downwards. Margins: Entire. Color: Variegated, irregular sized patches of coloration; the examples below are typical of leaves observed on plants of 'EM0002'. Example 1: Abaxial surface: A large center patch of 194A (greyish yellow green) flanking both sides of the mid rib and out to near the leaf margin, a wide patch of 157B (pale yellow green) at the apex and extending down along the margin to the base of the lobes. Adaxial surface: A large center patch of 138A (moderate yellow green) flanking both sides of the mid rib and out to near the margin with a narrow patch of 138A (moderate yellow green) along the mid rib and extending to the apex, small patches of 194A (greyish yellow green) in the center close to the mid rib, patches of 157A (pale yellow green) surrounding the lobes. Example 2: Abaxial surface: A patch of 138B (moderate yellow green) extending from one side of the mid rib and out to the margin and surrounding one lobe, with a small center patch of 194A (greyish yellow green), and patches of 155A (pale yellow green) along the apex and extending down along the margin to the base of the opposite lobe. Adaxial surface: A patch of NN137B to NN137C (greyish olive green) extending from one side of the mid rib and out to the margin and surrounding one lobe, with a patch of 194B (greyish yellow green) on one side of the leaf from the mid rib to the margin, and patches of 9D (pale greenish yellow) at the apex and extending down along the margin to the base of the opposite lobe. Example 3: Abaxial surface: A mottling of 145C to 145D (light yellow green) at the base with large patches of 138B (moderate yellow green) in the center on both sides of the mid rib and extending to the apex. Adaxial surface: Patches of 137A (moderate olive green) extending from both sides of the mid rib and out to the margin, a narrow patch of 144A (strong yellow green) in the center from one side of the mid rib and out to the margin, a patch of 1B to 1C (light greenish yellow) near the base above the lobe on the opposite side of the mid rib. Example 4: Abaxial surface: A large patch of 144A (pale yellow green) covering most of the leaf surface, with a narrow patch of 137C (moderate yellow green) along the margin on one side of the leaf. Adaxial surface: A patch of 144A (strong yellow green) covering most of the leaf surface, with narrow patches of 137B (moderate olive green) on one side of the mid rib and also along the margins of both lobes. Upper and lower surface leaf sheen: Lustrous. Venation: Pattern: Arcuate. Color, upper surface: Inconspicuous. Color, lower surface: 146A (moderate olive green).

*Petiole.*—Length: 3.18 cm to 3.81 cm on an immature leaf, about 5.08 cm on a mature leaf. Width: 0.64 cm at the point of attachment to the stem, narrowing towards the point of attachment to the leaf blade. Color: 146C (moderate yellow green).

*Aerial roots.*—One aerial root nodule present at each node, approximately 0.64 cm to 1.27 cm in length and colored 166A (greyish brown).

Inflorescence: None observed.

Cold tolerance: None observed.

Drought tolerance: None observed.

Disease and pest tolerance: None observed.

Fruit and seed set: None observed.

COMPARISON WITH PARENTAL VARIETY

'EM0002' differs from the parent pothos plant 'NJOY' in that 'EM0002' has leaves with more of a creamy yellow to yellow background coloration, whereas the background coloration of leaves of 'NJOY is whiter in appearance. Leaf coloration of 'EM0002' tends to become more mottled with age, whereas leaves of 'NJOY' become only slightly mottled with age. The leaf shape of 'EM0002' is predominantly cordate, whereas the leaf shape of 'NJOY' is predominantly ovate and sometimes deltate. Additionally, plants of 'EM0002' are less compact and more freely vining than plants of 'NJOY'.

COMPARISON WITH COMMERCIAL VARIETY

The parent variety 'NJOY' is the best commercial comparison to the new variety 'EM0002'.

I claim:

1. A new and distinct variety of *Epipremnum* plant named 'EM0002', substantially as illustrated and described herein.

* * * * *